(12) United States Patent
Fallin et al.

(10) Patent No.: US 7,766,943 B1
(45) Date of Patent: Aug. 3, 2010

(54) MODULAR PERCUTANEOUS SPINAL FUSION SYSTEM AND METHOD

(75) Inventors: T. Wade Fallin, Hyde Park, UT (US); Daniel F. Justin, Logan, UT (US)

(73) Assignee: Medicine Lodge Inc., Logan, UT (US)

( * ) Notice: Subject to any disclaimer, the term of this patent is extended or adjusted under 35 U.S.C. 154(b) by 783 days.

(21) Appl. No.: 11/464,161

(22) Filed: Aug. 11, 2006

Related U.S. Application Data

(60) Provisional application No. 60/708,006, filed on Aug. 11, 2005.

(51) Int. Cl.
*A61B 17/70* (2006.01)

(52) U.S. Cl. .................................... 606/264

(58) Field of Classification Search ................ 606/259, 606/260, 271, 261, 256, 266
See application file for complete search history.

(56) References Cited

U.S. PATENT DOCUMENTS

| | | | | |
|---|---|---|---|---|
| 5,180,393 A | * | 1/1993 | Commarmond | 623/13.14 |
| 5,360,431 A | | 11/1994 | Puno | |
| 5,387,213 A | * | 2/1995 | Breard et al. | 606/254 |
| 5,474,555 A | | 12/1995 | Puno | |
| 5,569,247 A | * | 10/1996 | Morrison | 606/264 |
| 5,591,166 A | * | 1/1997 | Bernhardt et al. | 606/266 |
| 6,083,226 A | * | 7/2000 | Fiz | 606/252 |
| 6,273,914 B1 | | 8/2001 | Papas | |
| 6,355,038 B1 | | 3/2002 | Pisharodi | |
| 6,379,354 B1 | * | 4/2002 | Rogozinski | 606/260 |
| 6,610,062 B2 | * | 8/2003 | Noblitt et al. | 606/261 |
| 6,626,904 B1 | * | 9/2003 | Jammet et al. | 606/266 |
| 6,626,909 B2 | | 9/2003 | Chin | |
| 6,669,697 B1 | | 12/2003 | Pisharodi | |
| 6,802,844 B2 | | 10/2004 | Ferree | |
| 2004/0102778 A1 | * | 5/2004 | Huebner et al. | 606/71 |
| 2005/0171539 A1 | * | 8/2005 | Braun et al. | 606/61 |
| 2005/0234454 A1 | * | 10/2005 | Chin | 606/61 |
| 2006/0089645 A1 | * | 4/2006 | Eckman | 606/61 |
| 2006/0265074 A1 | * | 11/2006 | Krishna et al. | 623/17.15 |
| 2007/0093838 A1 | * | 4/2007 | Khodadadyan-Klostermann et al. | 606/70 |

* cited by examiner

*Primary Examiner*—Thomas C Barrett
*Assistant Examiner*—Michael J Araj
(74) *Attorney, Agent, or Firm*—Peter K. Johnson; Barbara Daniels; G. Jo Hays

(57) ABSTRACT

A posterior spinal fusion system may include pedicle screws and one or more segments designed to be attached to the implanted pedicle screws via nuts to fuse spinal motion segments in a modular fashion. The pedicle screws may have semispherical receiving surfaces, and each segment may have mounting portions at both ends, with corresponding semispherical engagement surfaces. The nuts may also have semispherical surfaces. The semispherical surfaces permit polyaxial adjustment of the relative orientations of the segments and pedicle screws. Each mounting portion may have a passageway therethrough to receive the proximal end of the corresponding pedicle screw; each passageway may intersect the edge of the corresponding engagement surface to facilitate percutaneous placement. Such placement may be carried out through cannulae to provide a minimally invasive (MIS) implantation procedure.

7 Claims, 9 Drawing Sheets

MODULAR PERCUTANEOUS SPINAL FUSION SYSTEM AND METHOD

CROSS-REFERENCE TO RELATED APPLICATIONS

This application claims the benefit of:

U.S. Provisional Application No. 60/708,006, filed Aug. 11, 2005, which carries Applicants' docket no. MLI-43, and is entitled PEDICLE SCREW AND POLYAXIAL SECUREMENT SYSTEM FOR SPINAL POSTERIOR STABILIZATION.

The foregoing is incorporated herein by reference.

BACKGROUND OF THE INVENTION

1. The Field of the Invention

The present invention relates generally to implantable devices, and more precisely, to posterior spinal fusion systems.

2. The Relevant Technology

Many people experience joint pain in one form or another. In particular, back pain may result from the occurrence of a wide variety of spinal pathologies. Some such pathologies are currently treated by fusing adjacent vertebrae to prevent their relative motion. According to one known method, pedicle screws are implanted in the pedicles and are rigidly secured to a rod passing posterior to the pedicles.

Unfortunately, current procedures often involve the exposure of a relatively large area to permit implantation of the rod. Such exposure causes patient discomfort and lengthens the post-surgical healing time.

Some current procedures cannot be used to implant a rod that secures more than two vertebrae together. Other procedures can be used to fuse multiple vertebral levels, but such procedures often require difficult and potentially inaccurate rod contouring procedures to maintain the proper spinal curvature. Other known procedures are somewhat complex, and therefore require many parts and surgical steps. Accordingly, there is a need for new fusion systems and methods that remedy the shortcomings of the prior art.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to spinal fusion systems and methods that are modular and/or percutaneously implantable. The drawings and accompanying description are merely exemplary. Accordingly, the scope of the present invention is not intended to be limited by the examples discussed herein, but only by the appended claims.

Figure 1:
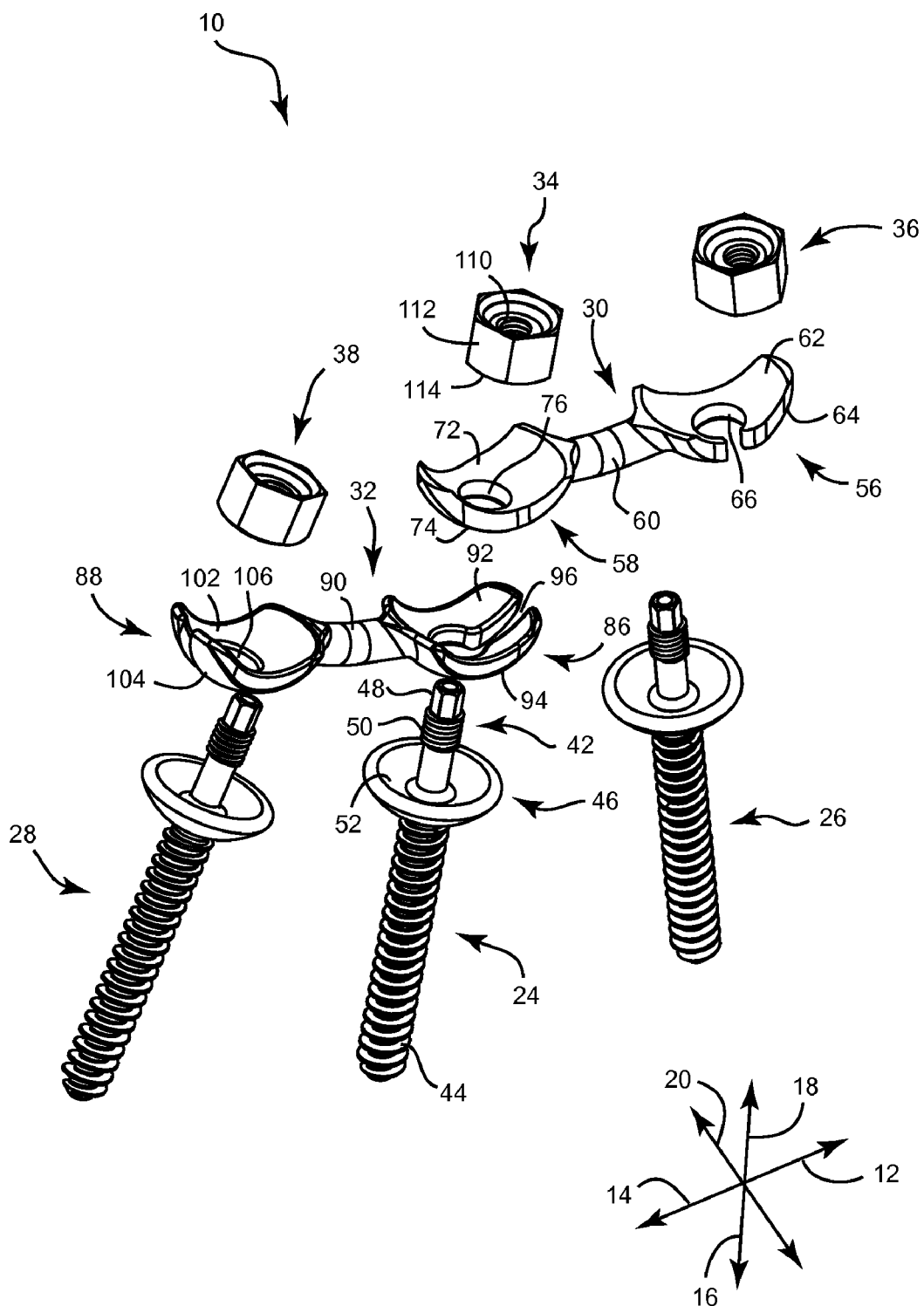
FIG. 1 is an exploded, perspective view of a spinal fusion system according to one embodiment of the invention.

Referring to FIG. 1, an exploded, perspective view illustrates a spinal fusion system 10 according to one embodiment of the invention. The spinal fusion system 10, or system 10, may be used for patients with chronic spinal problems including damaged intervertebral discs, spinal stenosis, facet degeneration, and spondylolisthesis. Arrows in FIG. 1 indicate the orientation of the system 10 upon implantation on the spine, with reference to conventional anatomical directions. More precisely, the arrows illustrate a cephalad direction 12, a caudal direction 14, an anterior direction 16, a posterior direction 18, and a medial/lateral axis 20.

As shown, the system 10 includes a first fixation member 24, a second fixation member 26, a third fixation member 28, a superior securement section 30, an inferior securement section 32, a first nut 34, a second nut 36, and a third nut 38. Since, in the embodiment of FIG. 1, the system 10 is designed for posterior fusion, i.e., fusion of vertebrae via attachment to their posterior aspects, each of the fixation members 24, 26, 28 may take the form of a pedicle screw. Accordingly, the fixation members 24, 26, 28 will hereinafter be termed first, second, and third pedicle screws 24, 26, and 28. Furthermore, since the system 10 is designed to provide modular fusion, i.e., fusion along a variable number of spinal motion segments, the first and second securement sections 32, 34 may be termed first and second segments 32, 34.

Each of the pedicle screws 24, 26, 28 may have a proximal end 42, a distal end 44, and a receiving flange 46 positioned between the proximal end 42 and the distal end 44. Each proximal end 42 may have a torque receiver 48 and a threaded portion 50. The torque receivers 48 are designed to be engaged by a distal end of a tool (not shown) so that torque can be transmitted from the tool to the pedicle screws 24, 26, 28 to drive the pedicle screws 24, 26, 28 into bone. The threaded portions 50 are designed to receive the nuts 34, 36, 38 so that the nuts 34, 36, 38 can secure the segments 30, 32 to the pedicle screws 24, 26 28 in a manner that will be shown and described subsequently.

The distal ends 44 are threaded so that the distal ends 44 can be threadably implanted in bone. The pedicle screws 24, 26, 28 may optionally be cannulated to facilitate guidance of the pedicle screws 24, 26, 28 into engagement with the vertebral pedicles via guide wires or other implements (not shown). The receiving flanges 46 protrude radially from the main bodies of the pedicle screws 24, 26, 28 to provide receiving surfaces 52 capable of attachment to the segments 30, 32 at multiple relative orientations. The receiving surfaces 52 may be semispherical, and in the embodiment of FIG. 1, the receiving surfaces 52 are also concave.

The cephalad segment 30 may have a cephalad mounting portion 56, a caudal mounting portion 58, and a stem 60. The cephalad mounting portion 56 is attachable to the second pedicle screw 26 and the caudal mounting portion 58 is attachable to the first pedicle screw 24. The stem 60 connects the cephalad mounting portion 56 to the caudal mounting portion 58. The stem 60 may optionally be deformable to permit adjustment of the relative positions and/or orientations of the mounting portions 56, 58. However, since the mounting portions 56, 58 are polyaxially adjustably attachable to the fixation members 24, 26, deformation of the stem 60 may not be needed.

As shown, the cephalad mounting portion 56 has a concave engagement surface 62 and a convex engagement surface 64. Each of the engagement surfaces 62, 64 has a semispherical shape capable of polyaxially adjustable engagement with a corresponding semispherical shape. More precisely, the concave engagement surface 62 may engage a convex surface with a similar radius of curvature at any of a plurality of relative orientations about three orthogonal axes. Similarly, the convex engagement surface 64 may engage a concave surface with a similar radius of curvature at any of a plurality of relative orientations about three orthogonal axes. If desired, the engagement surfaces 62, 64 may have substantially the same radius of curvature so that the cephalad mounting portion 56 is able to polyaxially adjustably engage a mounting portion similar to itself from either side.

The cephalad mounting portion 56 also has a passageway 66 capable of receiving the proximal end 42 of the second pedicle screw 26. The passageway 66 takes the form of a slot with a rounded interior end. The passageway 66 intersects the lateral edge of the cephalad mounting portion 56 so that the proximal end 42 can be inserted into the passageway 66 not only via relative anterior/posterior motion between the proximal end 42 and the passageway 66, but alternatively, via relative medial/lateral motion between the proximal end 42 and the passageway 66.

The caudal mounting portion 58 has a configuration somewhat similar to that of the cephalad mounting portion 56. More precisely, the caudal mounting portion 58 has a concave engagement surface 72 and a convex engagement surface 74. The engagement surfaces 72, 74 are semispherical and may optionally have the same radius of curvature. The caudal mounting portion 58 also has a passageway 76 capable of receiving the proximal end 42 of the first pedicle screw 24. However, unlike the passageway 66 of the cephalad mounting portion 56, the passageway 76 does not intersect the lateral edge of the caudal mounting portion 58. Rather, the passageway 76 is fully bounded. Thus, the proximal end 42 must be inserted into the passageway 76 via relative anterior/posterior motion between the proximal end 42 and the passageway 76.

The caudal segment 32 may be configured in a manner somewhat similar to that of the cephalad segment 30, and may be designed to operate in a similar manner. As shown, the caudal segment 32 also has a cephalad mounting portion 86, a caudal mounting portion 88, and a stem 90 that connects the mounting portions 86, 88 together.

The cephalad mounting portion 86 has a concave engagement surface 92, a convex engagement surface 94, and a passageway 96. Like the engagement surfaces 62, 64, 72, 74, the engagement surfaces 92, 94 may be substantially semispherical, and may have the same radius of curvature. The cephalad mounting portion 86 has a passageway 96 therethrough, which is capable of receiving the proximal end 42 of the first pedicle screw 24. Unlike the passageways 66, 76, the passageway 96 takes the form of a slot that intersects the cephalad edge of the cephalad mounting portion 86. Accordingly, the proximal end 42 can be inserted into the passageway 96 not only via relative anterior/posterior motion between the proximal end 42 and the passageway 96, but alternatively, via relative cephalad/caudal motion between the proximal end 42 and the passageway 96.

The caudal mounting portion 88 may be substantially identical to the caudal mounting portion 86. The caudal mounting portion 88 may thus have a concave engagement surface 102, a convex engagement surface 104, and a passageway 106, which are all substantially the same as their counterparts 92, 94, 96 of the cephalad mounting portion 86. Thus, the proximal end 42 of the third pedicle screw 28 can be inserted into the passageway 106 not only via relative anterior/posterior motion between the proximal end 42 and the passageway 106, but alternatively, via relative cephalad/caudal motion between the proximal end 42 and the passageway 106.

The nuts 34, 36, 38 are designed to engage the proximal ends 42 to press the associated mounting portions 56, 58, 86, 88 against the receiving flanges 46 of the corresponding pedicle screws 24, 26, 28. More specifically, each of the nuts 34, 36, 38 has a threaded bore 110, a polygonal perimeter 112, and a convex compression surface 114. The threaded bores 110 are designed to engage the threaded portions 50 of the proximal ends 42. The polygonal perimeters 112 are shaped to be engaged by a distal end of a tool (not shown) so that the tool can be used to rotate the threaded bores 110 into engagement with the threaded portions 50. The polygonal perimeters 112 may be hexagonal. The convex compression surfaces 114 may be substantially semispherical in shape, and may have a radius of curvature similar to those of the concave engagement surfaces 62, 72, 92, 102 of the segments 30, 32.

The system 10 may be assembled in multiple different configurations. As shown in FIG. 1, in one exemplary mode of assembly, the inferior segment 32 is first positioned such that the convex engagement surfaces 94, 104 engage the receiving surfaces 52 of the receiving flanges 46 of the first and third pedicle screws 24, 28. Then, the superior segment 30 is positioned such that the convex engagement surface 74 engages the concave engagement surface 92 of the cephalad mounting portion 86 of the inferior segment 32, and the convex engagement surface 64 engages the receiving surface 52 of the receiving flange 46 of the second pedicle screw 26.

Notably, the semispherical shapes of the engagement surfaces 62, 64, 72, 74, 92, 94, 102, 104 and receiving surfaces 52 enables the orientations of the segments 30, 32 to be polyaxially adjusted relative to each other and to the pedicle screws 24, 26, 28. This polyaxial adjustability is possible about any of three orthogonal axes for each engaging pair of semispherical surfaces. Thus, the configuration of the system 10 can be adjusted to suit a wide variety of spinal morphologies without requiring deformation of any of the components 24, 26, 28, 30, 32, 34, 36, 38 of the system. In this application, the phrase "polyaxially adjustability" refers to the ability of one member to be rotated relative to a second member in at least two orthogonal axes, and then attached to the second member in the selected relative orientation.

After the pedicle screws 24, 26, 28 and segments 30, 32 have been positioned and adjusted as described above, the nuts 34, 36, 38 are rotated into engagement with the threaded portions 50 and tightened to secure the segments, 30, 32 to the pedicle screws 24, 26, 28. More precisely, the nuts 34, 36, 38 press the convex engagement surfaces 94, 64, 104 against the receiving surfaces 52 of the first, second, and third pedicle screws 24, 26, 28, respectively, and press the convex engagement surface 74 against the concave engagement surface 92. Thus, further adjustment of the orientations of the segments 30, 32 is prevented, and the system 10 is made substantially rigid to prevent relative motion between the associated vertebrae.

Figure 2:
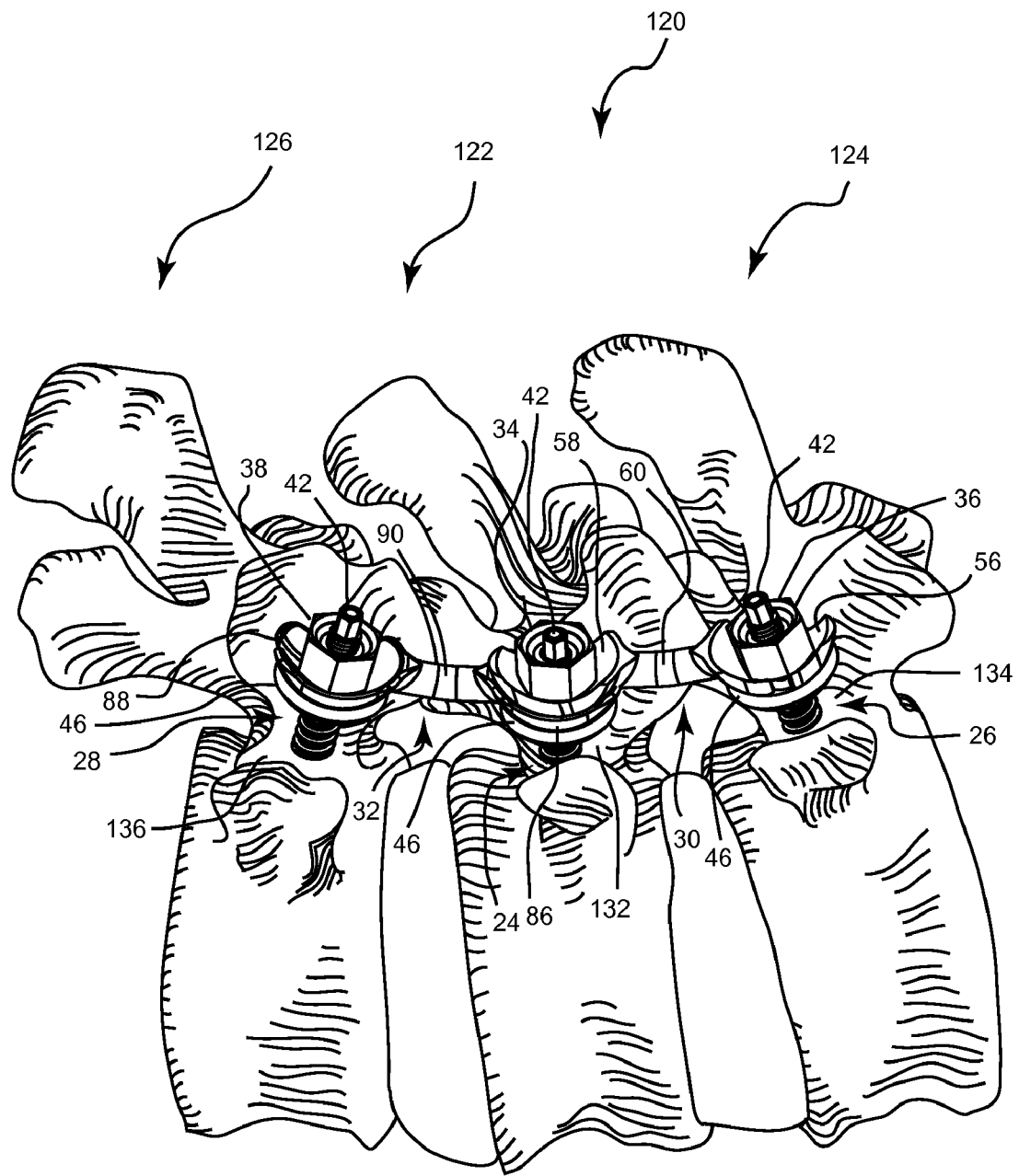
FIG. 2 is a perspective view of the spinal fusion system of FIG. 1 in fully-assembled form, secured to three vertebrae of a spine.
Figure 2:
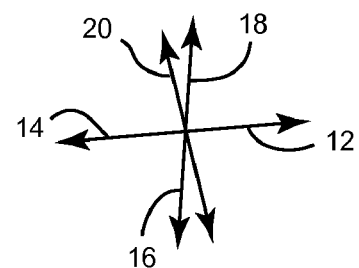

Referring to FIG. 2, a perspective view illustrates the spinal fusion system 10 of FIG. 1 in fully-assembled form, secured to a portion of a spine 120. The spine 120 has a first vertebra 122, a second vertebra 124 superior to the first vertebra 122, and a third vertebra 126 inferior to the first vertebra 122. The first vertebra 122 has a right pedicle 132, and second vertebra 124 has a right pedicle 134, and the third vertebra 126 has a right pedicle 136.

In order to secure the system 10 to the portion of the spine 120, the pedicle screws 24, 26, 28 may first be implanted in the pedicles 132, 134, 136, respectively, through the use of methods known in the art. If desired, guide wires (not shown) may first be implanted in the pedicles 132, 134, 136. The pedicles 132, 134, 136 may be reamed or otherwise resected to remove interfering bone. Then, the cannulated pedicle screws 24, 26, 28 may be inserted over the guide wires to facilitate implantation of the pedicle screws 24, 26, 28 into the pedicles 132, 134, 136. Once the pedicle screws 24, 26, 28 have been placed, the segments 30, 32 are placed and adjusted as described previously. Then, the nuts 34, 36, 38 are tightened on the proximal ends 42 to secure the segments 30, 32, as also described above.

FIG. 2 illustrates usage of the system 10 to provide only unilateral fixation. However, those of skill in the art will recognize that a similar system (not shown) may be also attached to the left pedicles (not visible) of the vertebrae 122, 124, 126 to provide bilateral fixation.

Figure 3:
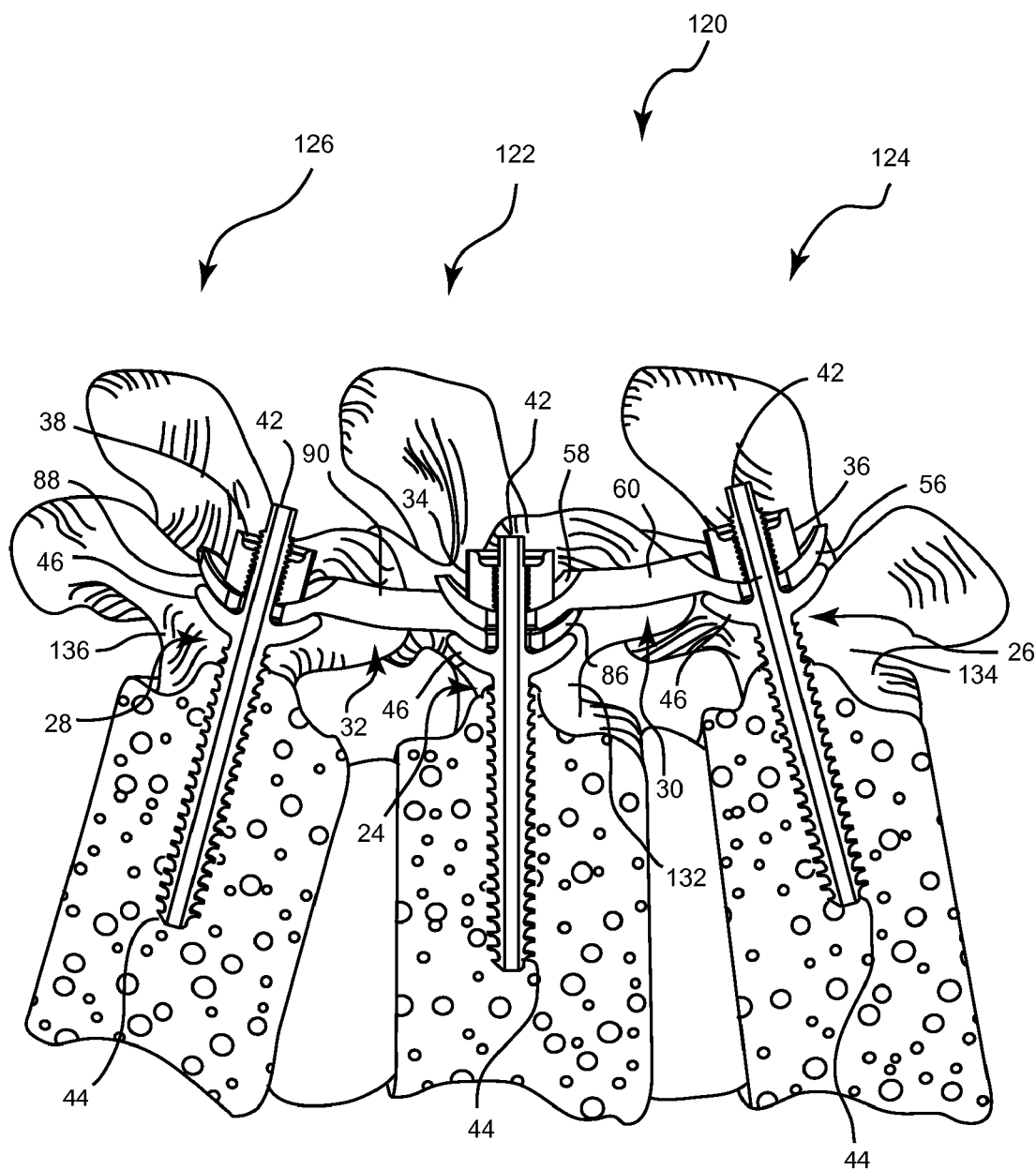
FIG. 3 is a side elevation, section view of the spinal fusion system and the vertebrae of FIG. 2.
Figure 3:
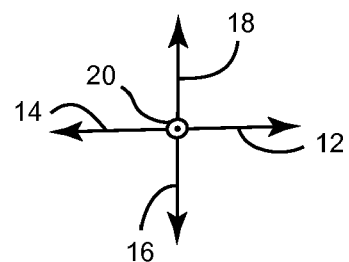

Referring to FIG. 3, a side elevation, section view illustrates the system 10 secured to the vertebrae 122, 124, 126 of FIG. 2. FIG. 3 shows the distal ends 44 of the pedicle screws 24, 26, 28, which are implanted in the pedicles 132, 134, 136 of the vertebrae 122, 124, 126. FIG. 3 also illustrates the manner in which the engagement surfaces 62, 64, 72, 74, 92, 94, 102, 104, the receiving surfaces 52, and the convex compression surfaces 114 engage each other. As in FIG. 2, the nuts 34, 36, 38 have been tightened so that the system 10 is substantially rigid, and the vertebrae 122, 124, 126 are unable to move relative to each other.

Figure 4:
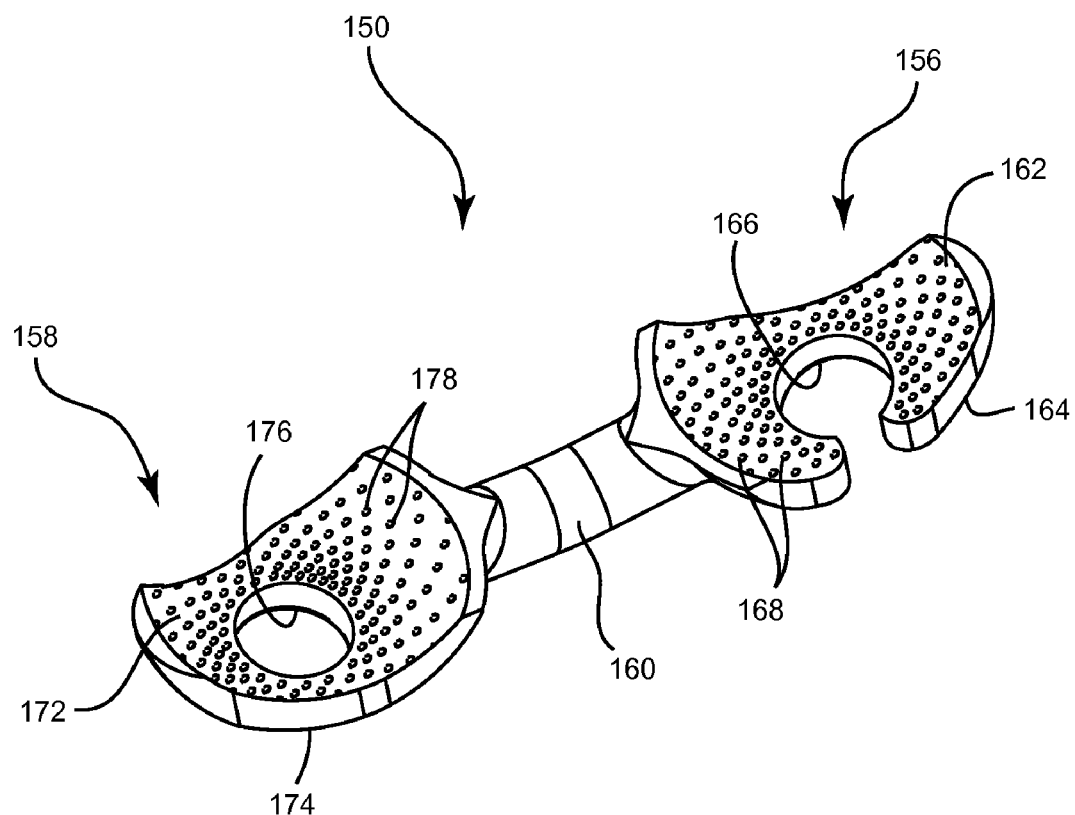
FIG. 4 is a perspective view of a segment of a spinal fusion system according to one alternative embodiment of the invention.

Referring to FIG. 4, a perspective view illustrates a segment 150 of a spinal fusion system (not shown) according to one alternative embodiment of the invention. As shown, the segment 150 has a shape similar to that of the superior segment 30 of the system 10 of FIG. 1. Accordingly, the segment 150 has a cephalad mounting portion 156, a caudal mounting portion 158, and a stem 160 that connects the mounting portions 156, 158 together.

The cephalad mounting portion 156 has a concave engagement surface 162 and a convex engagement surface 164, which may be substantially semispherical, and may have the same radius of curvature. The cephalad mounting portion 156 has a passageway 166 like the corresponding passageway 66 of the superior segment 30 of FIG. 1. Accordingly, the passageway 166 intersects a lateral edge of the cephalad mounting portion 156.

However, the concave engagement surface 162 differs from that of the superior segment 30 of FIG. 1 in that a plurality of surface irregularities 168 are present on the concave engagement surface 162. The surface irregularities 168 may take the form of bumps as shown, or may instead be divots, ridges, grooves, peaks, or any other features capable of enhancing frictional force between the concave engagement surface 162 and the surface it engages. If desired, features like the surface irregularities 168, or differently shaped features, may be present on the convex engagement surface 164 to enhance frictional engagement of the convex engagement surface 164.

The caudal mounting portion 158 has a concave engagement surface 172 and a convex engagement surface 174, which may be substantially semispherical, and may have the same radius of curvature. The caudal mounting portion 158 has a passageway 176 like the corresponding passageway 76 of the superior segment 30 of FIG. 1. Accordingly, the passageway 176 is fully bounded, and does not intersect any edge of the caudal mounting portion 158.

However, the concave engagement surface 172 differs from that of the superior segment 30 of FIG. 1 in that a plurality of surface irregularities 178 are present on the concave engagement surface 172. Like the surface irregularities 168, the surface irregularities 178 may take the form of bumps as shown, or may instead be divots, ridges, grooves, peaks, or any other features capable of enhancing frictional force between the concave engagement surface 172 and the surface it engages. If desired, features like the surface irregularities 178, or differently shaped features, may be present on the convex engagement surface 174 to enhance frictional engagement of the convex engagement surface 174.

If desired, the surface irregularities 168 and/or the surface irregularities 178 may provide a pattern of radial or otherwise evenly-spaced ridges, grooves, and/or other features that provide a clocking feature. Such a clocking feature may limit engagement of the corresponding engagement surfaces 162, 164, 172, 174 with their opposing surfaces to a plurality of discrete relative positions and/or orientations.

In any case, the surface irregularities 168, 178 may help to provide more secure engagement between the segment 150 and any other pedicle screws, nuts, and/or segments to which it is secured. Thus, the segment 150 may help resist slippage of the corresponding system after the system has been locked into the desired configuration.

Figure 5:
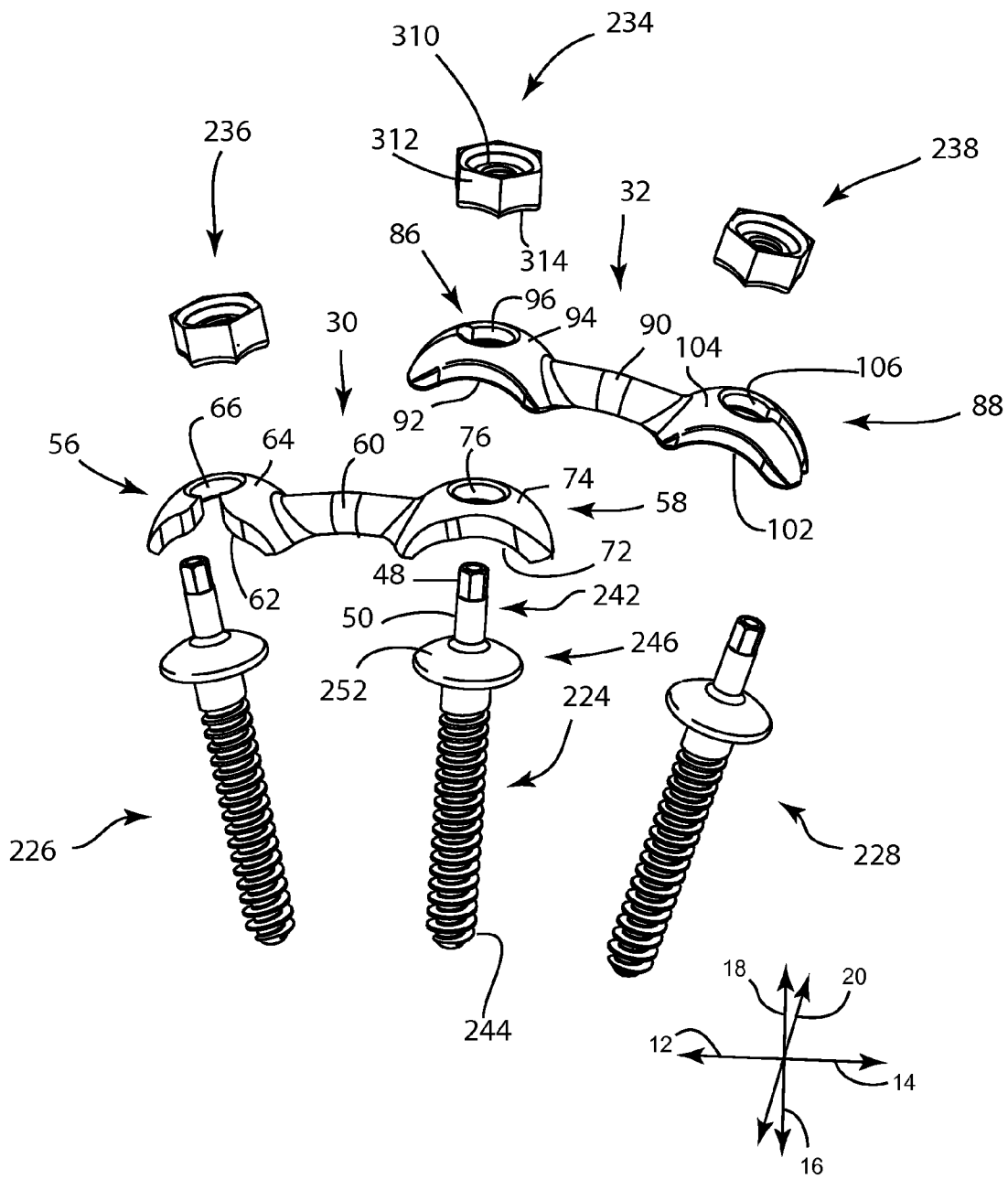
FIG. 5 is an exploded, perspective view of a spinal fusion system according to another alternative embodiment of the invention.

Referring to FIG. 5, an exploded, perspective view illustrates a spinal fusion system 210 according to another alternative embodiment of the invention. Like the system 10 of FIG. 1, the system 210 includes a first pedicle screw 224, a second pedicle screw 226, a third pedicle screw 228, a superior segment 30, an inferior segment 32, a first nut 234, a second nut 236, and a third nut 238. The segments 30, 32 may be identical to those of FIG. 1. Overall, the system 210 is similar to the system 10, except that in the system 210, the segments 30, 32 are oriented such that the concave engagement surfaces 62, 64, 72, 74, 92, 94, 102, 104 are oriented toward the pedicle screws 224, 226, 228.

As shown, each of the pedicle screws 224, 226, 228, has a proximal end 242, a distal end 244, and a receiving flange 246 between the proximal and distal ends 242, 244. Like the proximal ends 42 of the pedicle screws 24, 26, 28 of FIG. 1, each of the proximal ends 242 has a torque receiver 48 and a threaded portion 50. As in FIG. 1, the torque receivers 48 receive torque from a tool to facilitate implantation of the pedicle screws 224, 226, 228, and the threaded portions 50 threadably receive the nuts 234, 236, 238.

Each of the receiving flanges 246 has a receiving surface 252 with a substantially semispherical shape. However, unlike the receiving surfaces 52, the receiving surfaces 252 are convex. Therefore, the receiving surfaces 52 are shaped to engage the concave engagement surfaces 62, 72, 92, 102 of the segments 30, 32.

Like the nuts 34, 36, 38 of FIG. 1, each of the nuts 234, 236, 238 has a threaded bore 310 and a polygonal perimeter 312. However, in place of the convex compression surfaces 114, each of the nuts 234, 236, 238 has a concave compression surface 314. The concave compression surfaces 314 are shaped to engage the convex engagement surfaces 64, 74, 94, 104 of the segments 30, 32.

Like the system 10, the system 210 may be assembled in multiple different configurations. As shown in FIG. 5, the superior segment 30 may first be positioned such that the concave engagement surfaces 62, 72 engage the receiving surfaces 252 of the receiving flanges 246 of the first and second pedicle screws 224, 226. Then, the inferior segment 32 is positioned such that the concave engagement surface 92 engages the convex engagement surface 74 of the caudal mounting portion 58 of the superior segment 30, and the concave engagement surface 102 engages the receiving surface 252 of the receiving flange 246 of the third pedicle screw 228. As in FIG. 1, the semispherical shapes of the engagement surfaces 62, 64, 72, 74, 92, 94, 102, 104 and receiving surfaces 252 enables the orientations of the segments 30, 32 to be polyaxially adjusted relative to each other and to the pedicle screws 224, 226, 228.

After the pedicle screws 224, 226, 228 and segments 30, 32 have been positioned and adjusted as described above, the nuts 234, 236, 238 are rotated into engagement with the threaded portions 50 and tightened to secure the segments, 30, 32 to the pedicle screws 224, 226, 228. The nuts 234, 236, 238 then press the concave engagement surfaces 72, 62, 102 against the receiving surfaces 252 of the first, second, and third pedicle screws 224, 226, 228, respectively, and press the concave engagement surface 92 against the convex engagement surface 74. Thus, the system 210 is made substantially rigid to prevent relative motion between the associated vertebrae.

Either of the systems 10, 210 may be implanted in an open access surgical procedure. However, it may be desirable to use minimally-invasive surgical (MIS) techniques to reduce the disruption to surrounding tissues. Accordingly, it may be advantageous to implant one or more components of the systems 10, 210 percutaneously. "Percutaneous implantation" refers to motion of an implant to an implantation site within the body, in which at least some of the tissues covering the implantation site remain intact. FIGS. 6 through 9 illustrate one exemplary procedure for implanting a system similar to the system 210 percutaneously.

Figure 6:
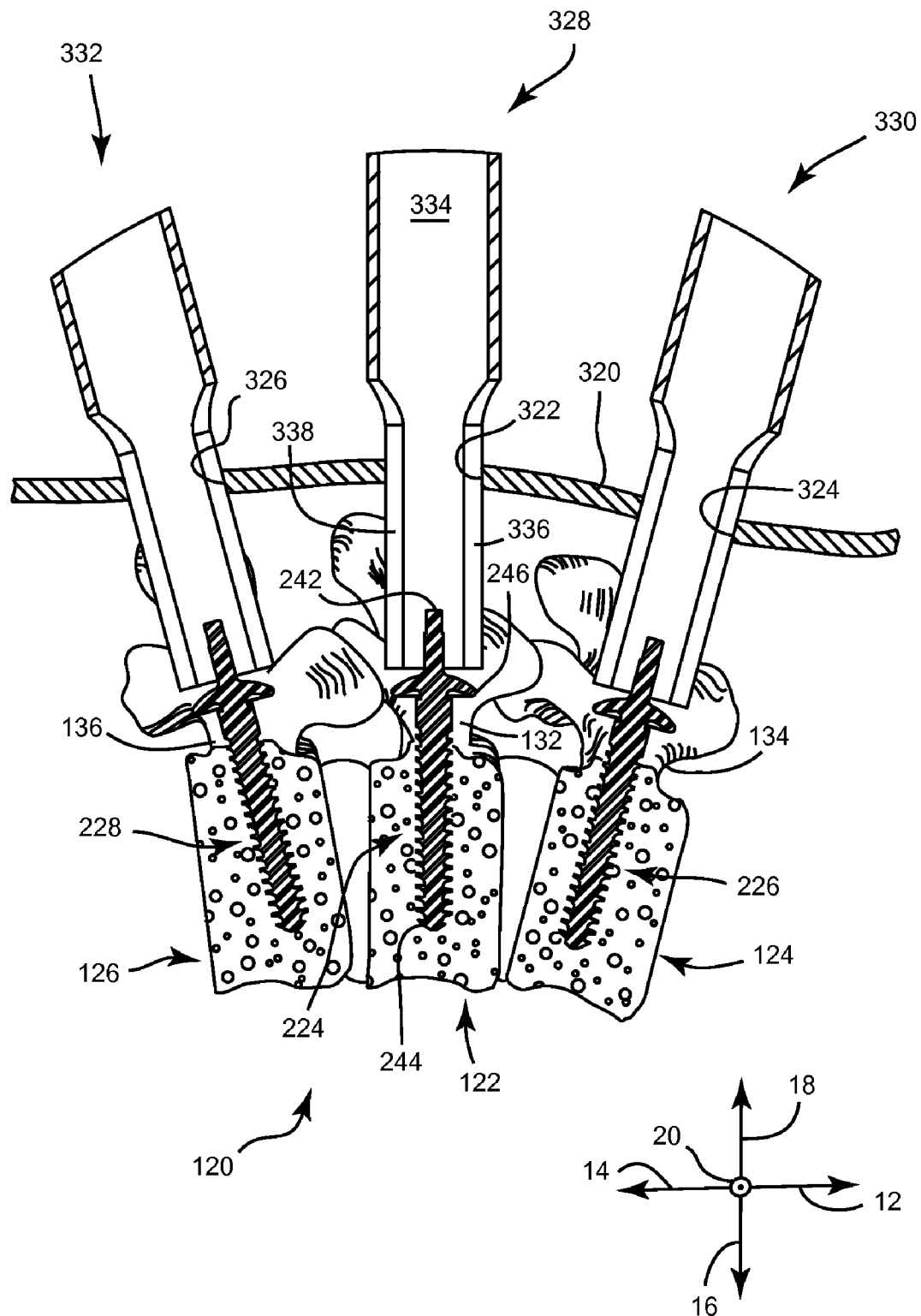
FIG. 6 is a side elevation, section view of a patient's lumbar region, with cannulae and the pedicle screws of the spinal fusion system of FIG. 5.

Referring to FIG. 6, a side elevation, section view illustrates a patient's lumbar region. As shown, the patient has skin 320, in which a first incision 322, a second incision 324, and a third incision 326 have been formed. The incisions 322, 324, 326 are appropriately sized to receive a first cannula 328, a second cannula 330, and a third cannula 332, respectively. Each of the cannulae 328, 330, 332 has a bore 334 extending along its length, a cephalad slot 336, and a caudal slot 338. The slots 336, 338 extend proximally from the distal ends of the cannulae 328, 330, 332. In the alternative to the cannulae 328, 330, 332, any type of cannula known in the art, and more particularly used for MIS surgery, maybe used.

As an initial step in the implantation method, guide wires (not shown) may be inserted through the skin at the sites where the incisions 322, 324, 326 are to be formed, and implanted into the pedicles 132, 134, 136 of the vertebrae 122, 124, 126, respectively. Dilators or other devices (not shown) may be used to widen the guide wire entry points to form the incisions 322, 324, 326. The distal ends of the cannulae 328, 330, 332 may then be inserted over the protruding proximal ends of the guide wires and through the incisions 322, 324, 326 to maintain access to the pedicles 132, 134, 136.

Once the cannulae 328, 330, 332 have been placed, the pedicle screws 224, 226, 228 of the system 210 of FIG. 5 may be implanted in the pedicles 132, 134, 136. More precisely, the first pedicle screw 224 may be inserted over the corresponding guide wire and through the first cannula 328 until the distal end 244 of the first pedicle screw 224 rests on the pedicle 132 of the first vertebra 122. The first pedicle screw 224 may then be rotated and urged toward the pedicle 132 through the use of a tool (not shown) until the first pedicle screw 224 has been implanted to the proper depth. The second and third pedicle screws 226, 228 may be implanted in the pedicles 134, 136 of the second and third vertebrae 124, 126 through the second and third cannulae 330, 332, respectively, through the use of similar procedures.

Figure 7:
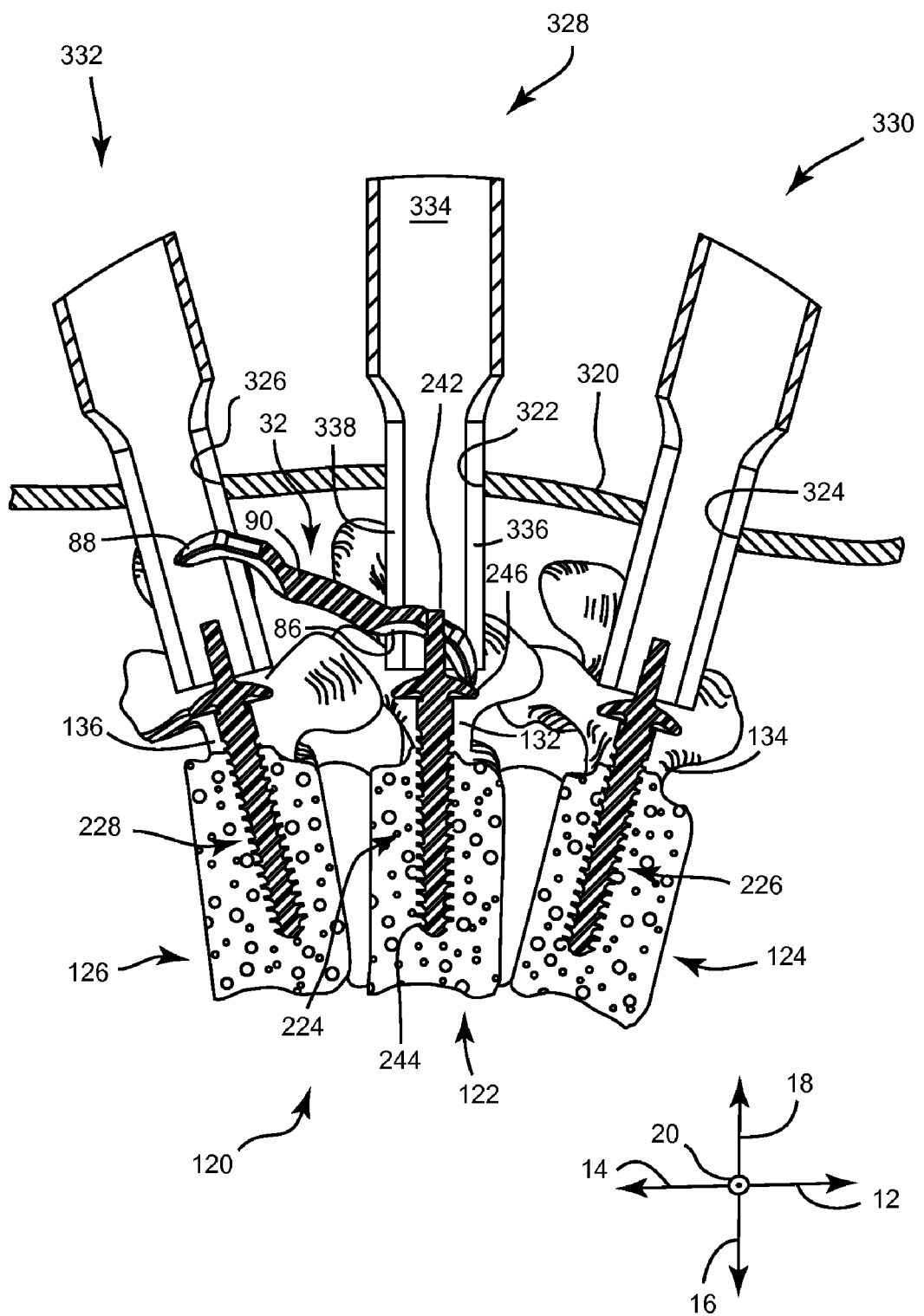
FIG. 7 is a side elevation, section view of the lumbar region and cannulae, with the pedicle screws and the first segment of the spinal fusion system of FIG. 5.

Referring to FIG. 7, a side elevation, section view illustrates the lumbar region, cannulae 328, 330, 332, and pedicle screws 224, 226, 228. After the pedicle screws 224, 226, 228 have been implanted in the pedicles 132, 134, 136, the inferior segment 32 may be inserted through the third cannula 332, with the cephalad mounting portion 86 leading. As the cephalad mounting portion 86 reaches the slots 336, 338 of the third cannula 332, the inferior segment 32 may be rotated such that the cephalad mounting portion 86 passes through the cephalad slot 336 of the third cannula 332, and into the first cannula 328 through the caudal slot 338 of the first cannula 328. This rotation may be accomplished through the use of a variety of implements (not shown), such as ramp formed in or inserted into the third cannula 332 to direct the cephalad mounting portion 86 toward the first cannula 328, or a rigid or articulating gripping tool that enables the surgeon to control the orientation of the inferior segment 32.

Since the passageway 96 of the cephalad mounting portion 86 intersects the cephalad edge of the cephalad mounting portion 86, the proximal end 42 of the first pedicle screw 224 is able to slide into the passageway 96 as the passageway 96 moves along the cephalad direction relative to the proximal end 42. The edge of the cephalad mounting portion 86 then slides along the receiving surface 252 of the first pedicle screw 224. The caudal mounting portion 88 may then be dropped onto the third pedicle screw 228 such that the proximal end 42 of the third pedicle screw 228 enters the passageway 106 of the caudal mounting portion 88.

Figure 8:
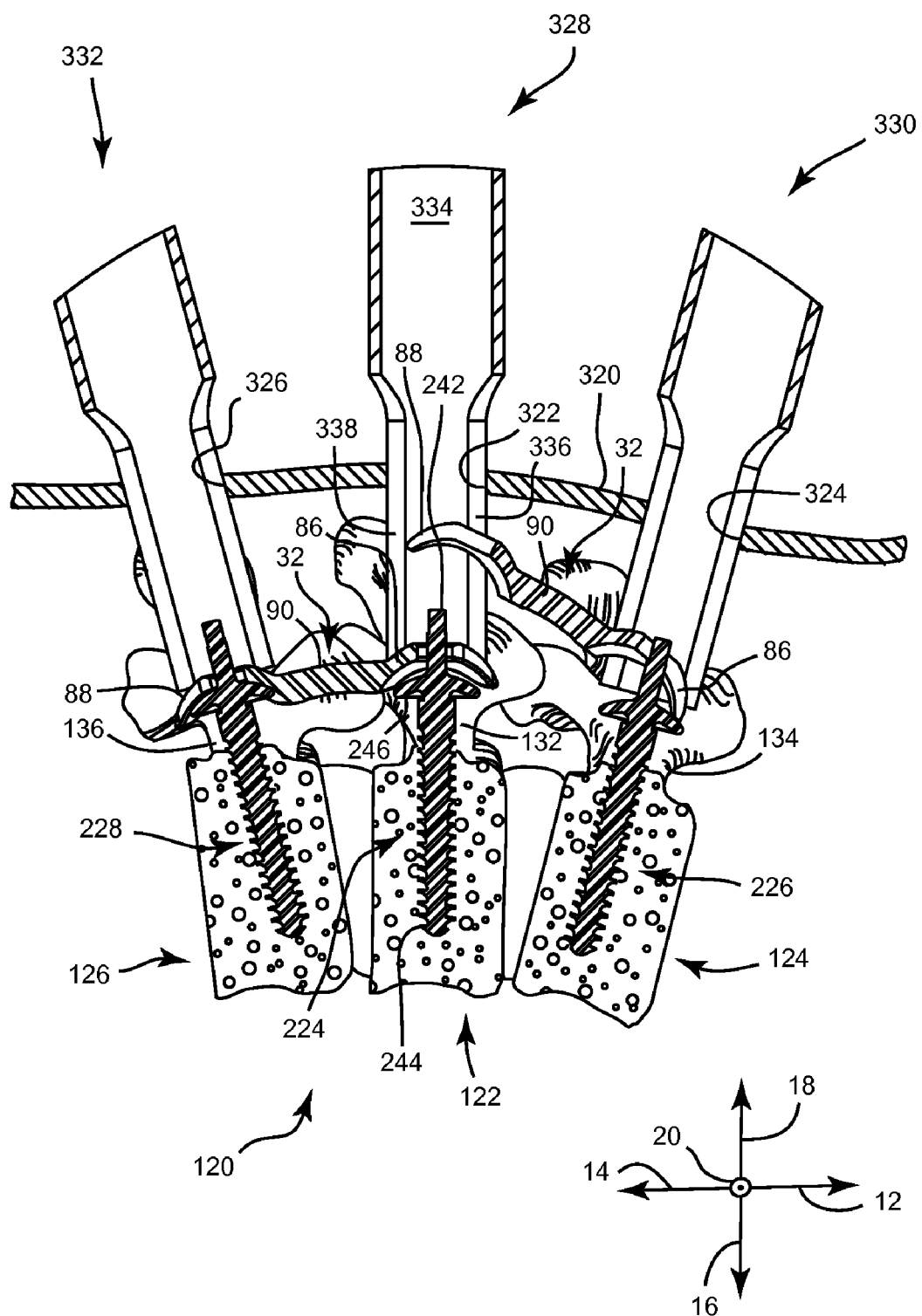
FIG. 8 is a side elevation, section view of the lumbar region and cannulae, with the pedicle screws and the inferior segment of the spinal fusion system of FIG. 5, and an additional segment similar to the inferior segment.

Referring to FIG. 8, a side elevation, section view illustrates the lumbar region and cannulae 328, 330, 332, with the pedicle screws 224, 226, 228 and the inferior segment 32 in place. After the inferior segment 32 has been positioned as described above, an additional segment substantially identical to the inferior segment 32 may be inserted through the first cannula 328, with the cephalad mounting portion 86 leading. The segment 32 may then be positioned on the first and second pedicle screws 224, 226 in substantially the same manner as the inferior segment 32 that has already been implanted to rest on the first and third pedicle screws 224, 228.

More precisely, as the cephalad mounting portion 86 reaches the slots 336, 338 of the first cannula 328, the inferior segment 32 may be rotated such that the cephalad mounting portion 86 passes through the cephalad slot 336 of the first cannula 328, and into the second cannula 330 through the caudal slot 338 of the second cannula 330. The proximal end 42 of the second pedicle screw 226 is able to slide into the passageway 96 of the cephalad mounting portion 86 as the passageway 96 moves along the cephalad direction relative to the proximal end 42. The edge of the cephalad mounting portion 86 then slides along the receiving surface 252 of the second pedicle screw 226. The caudal mounting portion 88 may then be dropped onto the cephalad mounting portion 86 of the previously implanted inferior segment 32 such that the proximal end 42 of the first pedicle screw 224 enters the passageway 106 of the caudal mounting portion 88.

Figure 9:
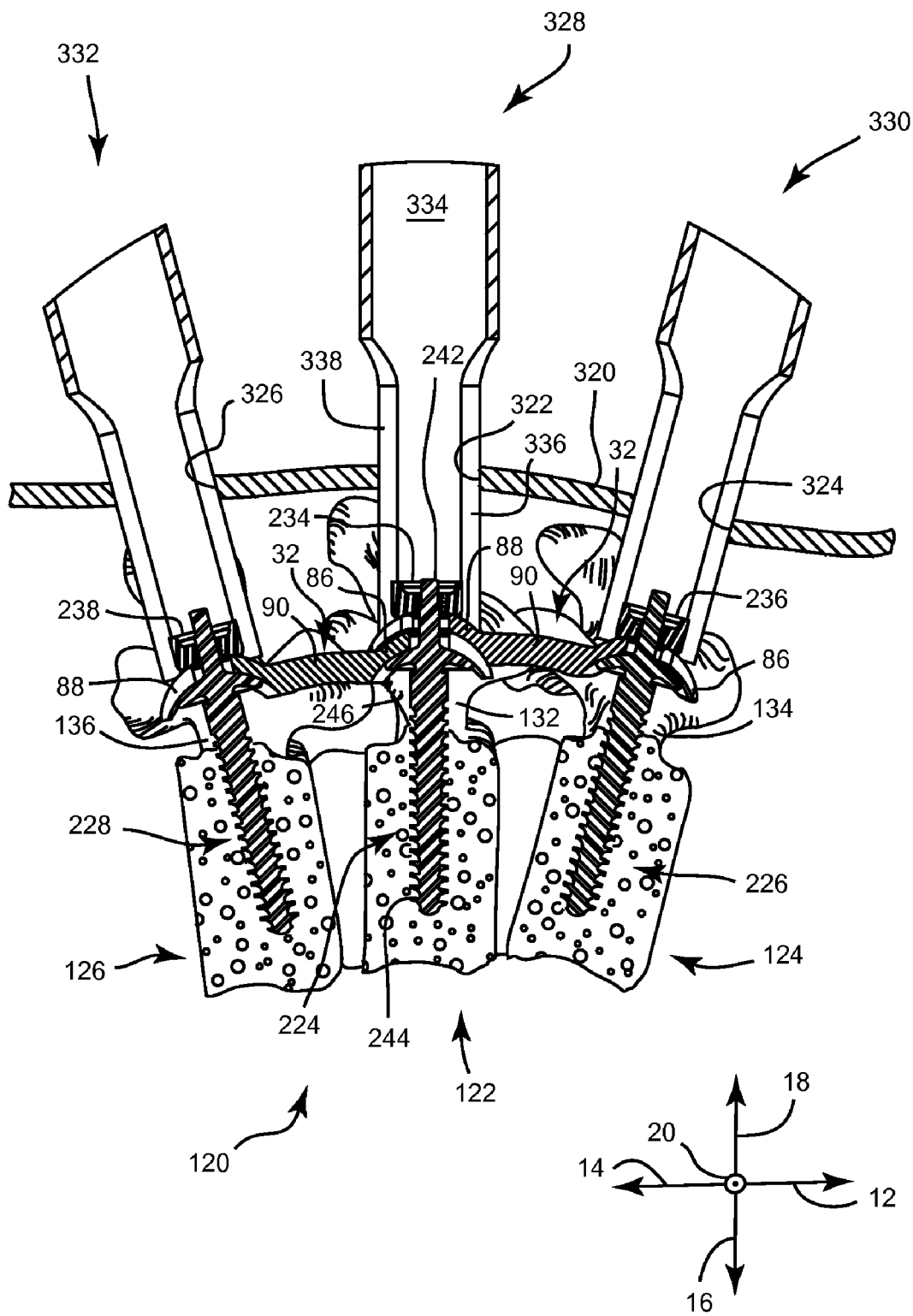
FIG. 9 is a side elevation, section view of the lumber region and cannulae, with the entire spinal fusion system of FIG. 5 in place on the vertebrae of the lumbar region, except that the superior segment of FIG. 5 has been replaced by the additional segment.

Referring to FIG. 9, a side elevation, section view illustrates the lumber region and cannulae 328, 330, 332, with the entire spinal fusion system in place. After the inferior segment 32 and the additional segment 32 have been positioned relative to the pedicle screws 224, 226, 228 and adjusted to their proper orientations relative to each other and the pedicle screws 224, 226, 228, the nuts 234, 236, 238 may be applied to secure the inferior segment 32 and the additional segment 32 to the pedicle screws 224, 226, 228.

More specifically, the first nut 234 may be inserted through the first cannula 328 such that the threaded bore 310 of the first nut 234 receives the threaded portion 50 of the proximal end 42 of the first pedicle screw 224. The first nut 234 is then tightened. In similar fashion, the second and third nuts 236, 238 are inserted through the second and third cannulae 330, 332 and tightened on the threaded portions 50 of the proximal ends 42 of the second and third pedicle screws 226, 228. Thus, the fixation system is substantially rigid, and further adjustment between any of the receiving surfaces 252 and the engagement surfaces 92, 94, 102, 104 is substantially prevented.

The cannulae 328, 330, 332 are then removed from the incisions 322, 324, 326, respectively, and the incisions 322, 324, 326 are closed to permit the implantation site to commence healing. Those of skill in the art will recognize that FIGS. 6 through 9 illustrate only one of many potential MIS procedures. Such procedures may be used with a wide variety of embodiments, including the systems 10, 210 of FIGS. 1 and 5 and the segment 150 of FIG. 4.

The foregoing description discloses a number of different elements that may be combined in various ways to provide a number of alternative implantable systems. Although the foregoing examples relate to implantation of a posterior spinal fusion system, the present invention may be applied to a wide variety of implants, within and outside the orthopedic area.

The present invention may be embodied in other specific forms without departing from its spirit or essential characteristics. It is appreciated that various features of the systems and methods described above can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method comprising:
   implanting a first fixation member in a first vertebra;
   positioning an engagement surface of a caudal mounting portion of a superior segment into engagement with an engagement surface of a cephalad mounting portion of an inferior segment;
   polyaxially adjusting the engagement surface of the caudal mounting portion of the superior segment relative to the engagement surface of the cephalad mounting portion of the inferior segment while the engagement surfaces are in engagement with one another;
   attaching the caudal mounting portion to the first fixation member;
   attaching the cephalad mounting portion to the first fixation member;
   implanting a second fixation member in a second vertebra superior to the first vertebra;
   implanting a third fixation member in a third vertebra inferior to the first vertebra;
   attaching a cephalad mounting portion of the superior segment to the second fixation member to substantially prevent relative motion between the first and second vertebrae; and
   attaching a caudal mounting portion of the inferior segment to the third fixation member to substantially prevent relative motion between the first and third vertebrae.

2. The method of claim 1, wherein the caudal mounting portions of the superior and inferior segments have substantially the same shape and the cephalad mounting portions of the superior and inferior segments have substantially the same shape.

3. The method of claim 1, further comprising:
   polyaxially adjustably engaging the engagement surface of the cephalad mounting portion of the superior segment with an engagement surface of a caudal mounting portion of an additional segment; and
   attaching the caudal mounting portion of the additional segment to the second fixation member.

4. The method of claim 1, wherein at least one of the engagement surfaces comprises at least one surface irregularity, wherein attaching the caudal and cephalad mounting portions to the first fixation member comprises urging the engagement surfaces together such that the surface irregularity restricts relative motion between the engagement surfaces.

5. The method of claim 1, wherein the first fixation member comprises a pedicle screw, wherein implanting the first fixation member in the first vertebra comprises implanting the pedicle screw in a pedicle of the first vertebra, the method further comprising positioning the superior and inferior segments to bridge intervertebral spaces between the pedicle of the first vertebra and pedicles of two vertebrae adjacent to the first vertebra.

6. The method of claim 1, further comprising:
   inserting the superior segment through a cannula; and
   inserting the inferior segment though a cannula.

7. The method of claim 1,
   wherein polyaxially adjusting the engagement surfaces comprises adjusting at least one of the superior segment and the inferior segment through a cannula.

* * * * *